(12) United States Patent
Kulanthaivel et al.

(10) Patent No.: US 6,630,147 B1
(45) Date of Patent: Oct. 7, 2003

(54) PSEUDOMYCIN NATURAL PRODUCTS

(75) Inventors: Palaniappan Kulanthaivel, Carmel, IN (US); Matthew David Belvo, Greenfield, IN (US); James William Martin, Coatesville, IN (US); Thomas John Perun, Indianapolis, IN (US); Douglas Joseph Zeckner, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/958,995

(22) PCT Filed: Apr. 14, 2000

(86) PCT No.: PCT/US00/08727

§ 371 (c)(1),
(2), (4) Date: Oct. 15, 2001

(87) PCT Pub. No.: WO00/63237

PCT Pub. Date: Oct. 26, 2000

Related U.S. Application Data
(60) Provisional application No. 60/129,447, filed on Apr. 15, 1999.

(51) Int. Cl.[7] .................. A61K 39/00; A61K 39/38; A61K 39/108; A61K 38/00; C07K 16/00
(52) U.S. Cl. .............. 424/184.1; 424/234.1; 424/260.1; 514/11; 514/15; 530/300; 530/317; 530/328
(58) Field of Search .............. 424/184.1, 234.1, 424/260.1; 514/11, 15; 530/300, 317, 328

(56) References Cited

U.S. PATENT DOCUMENTS 5,576,298 A   11/1996   Strobel et al.
5,837,685 A   11/1998   Strobel et al.

OTHER PUBLICATIONS

A. Ballio, et al., *Febs Letters*, NL, Elsevier Science Publishers, Amsterdam, 355:1, 96–100 (1994).

*Primary Examiner*—Mark Navarro
(74) *Attorney, Agent, or Firm*—Tina M. Tucker

(57) ABSTRACT

The invention relates to pseudomycin natural products including pseudomycins A' and B', methods for making such pseudomycins, and methods employing antifungal activity of these pseudomycins. NMR and mass spectrometry indicate a formula for pseudomycin A' of:

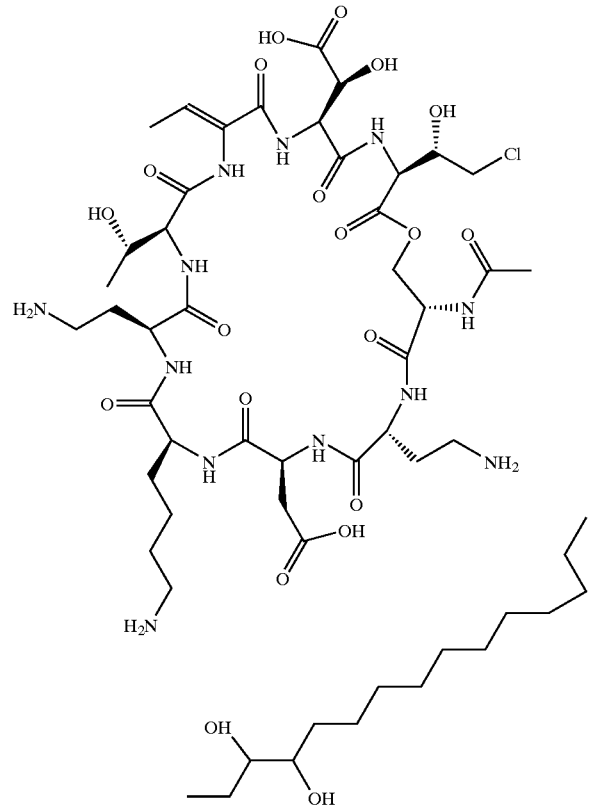

NMR and mass spectrometry indicate a formula for pseudomycin B' of:

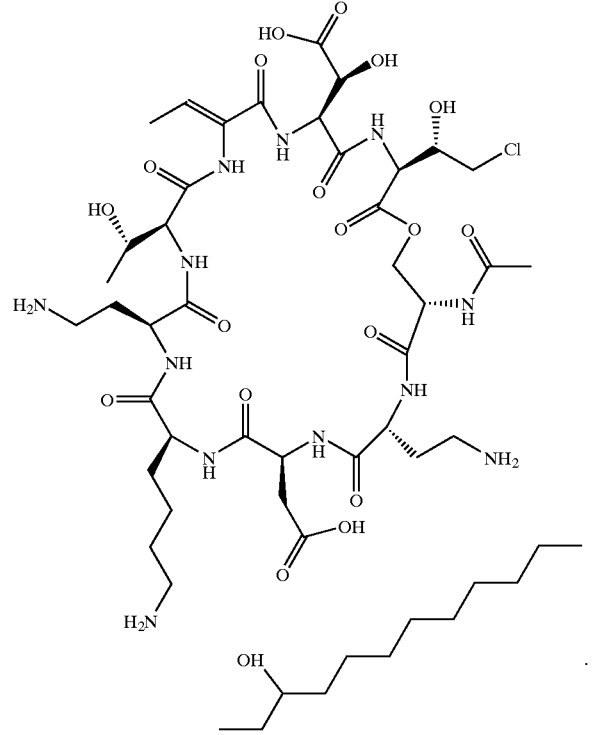

2 Claims, No Drawings

PSEUDOMYCIN NATURAL PRODUCTS

This application is the national phase of PCT/US00/08727, filed Apr. 14, 2000, which claims benefit of U.S. provisional application No. 60/129,447, filed Apr. 15, 1999.

FIELD OF THE INVENTION

The present invention relates to pseudomycin natural products including pseudomycins A' and B', methods for making such pseudomycins, and methods employing antifungal activity of these pseudomycins.

BACKGROUND

Fungal infections are a significant cause of disease, degradation of quality of life, and mortality among humans, particularly for immune compromised patients. The incidence in fungal infections in humans has increased greatly in the past 20 years. This is in part due to increased numbers of people with immune systems weakened or devastated by organ transplants, cancer chemotherapy, AIDS, age, and other similar disorders or conditions. Such patients are prone to attack by fungal pathogens that are prevalent throughout the population but are kept in check by a functioning immune system. These pathogens are difficult to control because some existing antifungal agents are either highly toxic or only inhibit fungal activity. For example, the polyenes are fungicidal but toxic; whereas, the azoles are much less toxic but only fungistatic. More importantly, there have been recent reports of azole and polyene resistant strains of Candida which severely limits therapy options against such strains.

*Pseudomonas syringae* produce several classes of antifungal or antibiotic agents, such as the pseudomycins, syringomycins, syringotoxins, and syringostatins, which are lipodepsinonapeptides. Natural strains and transposon generated mutants of *P. syringae* produce these lipodepsinonapeptides. Several of the pseudomycins, syringomycins and other lipodepsipeptide antifungal agents have been isolated, chemically characterized, and shown to possess wide spectrum antifungal activity, including activity against important fungal pathogens in both humans and plants. For example, pseudomycins A, B, C and C' have each been isolated and purified and their structures have been characterized by methods including amino acid sequencing, NMR, and mass spectrometry. See. e.g. Ballio et al., "Novel bioactive lipodepsipeptides from *Pseudomonas syringae*: the pseudomycins," *FEBS Lett*. 355. 96–100 (1994) and U.S. Pat. No. 5,576,298. The pseudomycins, the syringomycins, the syringotoxins, and the syringostatins represent structurally distinct families of antifungal compounds.

None of the pseudomycins, syringomycins, syringotoxins, or syringostatins has been brought to market for antifungal therapy. Discovery of undesirable side effects, making formulations, scaling up production, and other development problems have thus far prevented exploitation of the pseudomycins, syringomycins, syringotoxins, or syringostatins against the full range of fungal infections that affect animals, humans and plants. There remains a need for an antifungal agent that can be used against infections not treated by existing antifungal agents and for application against infections in animals, humans, or plants.

SUMMARY OF THE INVENTION

The present invention provides a pseudomycin natural product produced by *P. syringae*. The pseudomycin natural product includes a depsinonapeptide ring with the sequence Ser-Dab-Asp-Lys-Dab-aThr-Dhb-HOAsp-ClThr, more specifically, L-Ser-D-Dab-L-Asp-L-Lys-L-Dab-L-aThr-Z-Dhb-L-Asp(3-OH)-L-Thr(4-Cl), with the carboxyl group of the ClThr and the hydroxyl group of the serine closing the ring with a lactone bond. Pseudomycin A' (IA) includes a 3,4-dihydroxypentadecanoic acid moiety, the carboxyl group of which forms an amide bond with the amine group of the N-terminal serine.

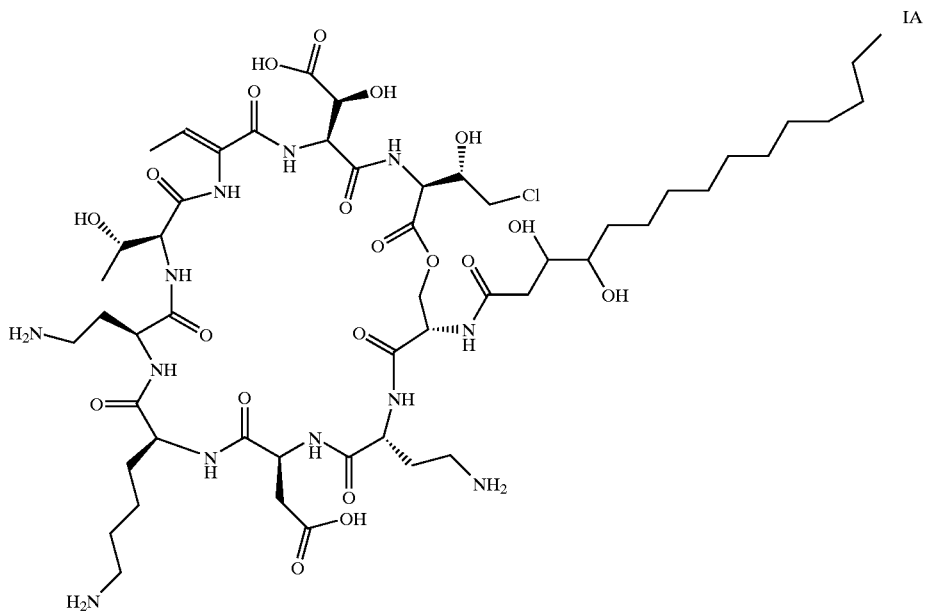

IA

Pseudomycin B' (IB) includes a 3-hydroxydodecanoic acid moiety, the carboxyl group of which forms an amide bond with the amine group of the N-terminal serine.

IB

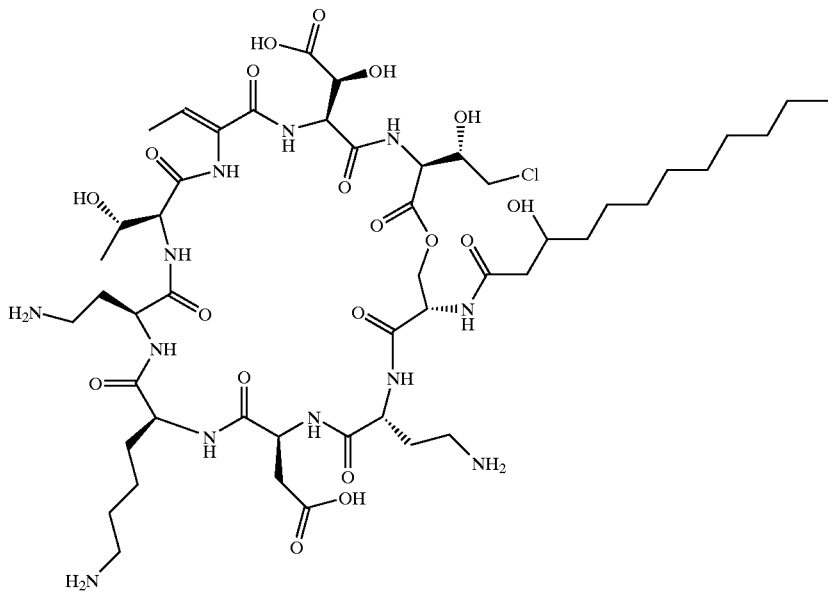

The invention also relates to methods employing a pseudomycin natural product, such as pseudomycin A', pseudomycin B' or a mixture thereof, for inhibiting fungal activity or for reducing the symptoms of a fungal infection in a patient in need thereof. Such methods can kill the fungus, decrease the burden of a fungal infection, reduce fever and/or increase the general well being of a patient. The methods of the invention are effective against fungi such as *Candida parapsilosis, Candida albicans, Cryptococcus neoformans,* and/or *Histoplasma capsulatum.*

DETAILED DESCRIPTION

Pseudomycins

As used herein, pseudomycin or pseudomycin natural product refers to one or more members of a family of antifungal agents that has been isolated from the bacterium *Pseudomonas syringae*. A pseudomycin is a lipodepsipeptide, a cyclic peptide including one or more unusual amino acids and having one or more appended hydrophobic or fatty acid side chains. Specifically, the pseudomycins are lipodepsinonapeptides, with a cyclic peptide portion closed by a lactone bond and including the unusual amino acids 4-chlorothreonine, 3-hydroxyaspartic acid, dehydro-2-aminobutyric acid, and 2,4-diaminobutyric acid. It is believed that these unusual amino acids are involved in biological characteristics of the pseudomycins, such as stability in serum and their killing action.

Each pseudomycin has the same cyclic peptide nucleus, but they differ in the hydrophobic side chain attached to this nucleus. Each pseudomycin has a cyclic nonapeptide ring having the sequence Ser-Dab-Asp-Lys-Dab-aThr-Dhb-HOAsp-ClThr (i.e., Serine; 2,4-Diaminobutyric acid; Aspartic acid; Lysine; 2,4-Diaminobutyric acid; alloThreonine; Dehydro-2-aminobutyric acid; 3-hydroxyAspartic acid; 4-chloroThreonine), with the carboxyl group of the ClThr and the hydroxyl group of the serine closing the ring with a lactone bond. The lipophilic moiety is attached to the amine group of the N-terminal serine. The amine group of the serine forms an amide bond with the carboxyl of a 3,4-dihydroxytetradecanoyl moiety in pseudomycin A, a 3-monohydroxytetradecanoyl moiety in pseudomycin B, a 3,4-dihydroxyhexadecanoyl moiety in pseudomycin C and a 3-monohydroxyhexadecanoyl moiety in pseudomycin C'. The carboxyl group of the serine forms an amide bond with the Dab of the ring.

Pseudomycins A' and B'

As used herein the terms pseudomycin A' and pseudomycin B' refer to antifungal agents that have been isolated from the bacterium *Pseudomonas syringae*. Pseudomycins A' and B' are pseudomycins having the characteristic depsinonapeptide ring with the sequence Ser-Dab-Asp-Lys-Dab-aThr-Dhb-HOAsp-ClThr, with the carboxyl group of the ClThr and the hydroxyl group of the serine closing the ring with a lactone bond. Pseudomycin A' includes a 3,4-dihydroxypentadecanoic acid moiety, the carboxyl group of which forms an amide bond with the amine group of the N-terminal serine. Pseudomycin B' includes a 3-hydroxydodecanoic acid moiety, the carboxyl group of which forms an amide bond with the amine group of the N-terminal serine.

Biological Activities of Pseudomycins

A pseudomycin has several biological activities including killing various fungi, such as fungal pathogens of plants and animals. In particular, a pseudomycin is an active antimycotic agent against fungi that cause opportunistic infections in immune compromised individuals. These fungi include various species of Candida including *C. parapsilosis, C. albicans, C. glabrata, C. tropicalis,* and *C. krusei.* They also incldue other genera such as *Cryptococcus neoformans, Aspergillus fumigatus,* and *Histoplasma capsulatum.* Killing, rather than inhibiting the growth of fungi, particularly of fungal pathogens, is a desirable and preferred biological activity of an antifungal, such as pseudomycin A' and/or B'.

The pseudomycins have been shown to be toxic to a broad range of plant-pathogenic fungi including *Rynchosporium secalis, Ceratocystis ulmi, Rizoctonic solani, Sclerotinia sclerotiorum, Verticillium albo-atrum, Verticillium dahliae, Thielaviopis basicola, Fusarium oxysporum* and *Fusarium culmorum.* (see Harrison, L., et al., "Pseudomycins, a family of novel peptides from *Pseudomonas syringae* possessing broad-spectrum antifungal activity," *J. of General*

*Microbiology,* 7, 2857–2865 (1991).) In addition, *P. syringae* MSU 16H has been shown to confer a greater protection than the wild-type strain in elms infected with *Ceratocystic ulmi,* the causal agent of Dutch elm disease. (see e.g., Lam et al. *Proc. Natl. Sci. USA,* 84, 6447–6451 (1987)).

Pseudomonas syringae

*Pseudomonas syringae* include a wide range of bacteria that are generally associated with plants. Some of the *P. syringae* are plant pathogens, while others are only weakly pathogenic or are saprophytes. Many different isolates of *P. syringae* produce one or more cytotoxic agents that can help this bacterium survive in the wild where it must compete with fungi and other bacteria. The cytotoxic agents produced by *P. syringae* include anti-fungal agents such as the pseudomycins, the syringomycins, the syringotoxins, and the syringostatins.

Strains of *P. syringae* that produce one or more pseudomycins have been described in the art. For example, wild type strain MSU 174 (isolated from a Montana barley field) and a mutant of this strain generated by transposon mutagenesis using TN905 (MSU 16H) are described in U.S. Pat. No. 5,576,298, issued Nov. 19, 1996 to G. Strobel et al.; Harrison et al., J. "Pseudomycins, a family of novel peptides from *Pseudomonas syringae* possessing broad-spectrum antifungal activity," *Gen. Microbiology* 137, 2857–2865 (1991); and Lamb et al., "Transposon mutagenesis and tagging of fluorescent pseudomonas: Antimycotic production is necessary for control of Dutch elm disease," *Proc. Natl. Acad. Sci. USA* 84, 6447–6451 (1987). Methods for growth of various strains of *P. syringae* and their use in production of anti-fungal agents such as pseudomycins are also disclosed in U.S. patent application Ser. No. 09/958,996 by Matthew D. Hilton et al. entitled "Pseudomycin Production By *Pseudomonas Syringae*" submitted evendate herewith and described below. Cultures of MSU 174 and MSU 16H are on deposit at Montana State University (Bozeman, Mont., USA) and available from the American Type Culture Collection (Parklawn Drive, Rockville, Md., USA). The disclosures of the references cited in this paragraph are incorporated herein by reference.

The present invention includes a strain, an isolate, and a biologically-purified culture of *P. syringae* that produces pseudomycin A' and/or B', in amounts at least about 10 $\mu$g/mL. Preferably, the biologically-purified culture of a microorganism is of *Pseudomonas syringae* strain MSU 16H, 25-B1, 67H1, or 7H9-1, or a mutant, variant, isolate, or recombinant of these strains that produces pseudomycin A' and/or B'. Cultures MSU 174 and MSU 16H were obtained as described in the references cited herein above.

A strain of *P. syringae* that is suitable for production of pseudomycin A' and/or B' can be isolated from environmental sources including plants, such as barley plants, citrus plants, and lilac plants, and also from sources such as soil, water, air, and dust. A preferred strain is isolated from plants. Strains of *P. syringae* that are isolated from environmental sources can be referred to as wild type. As used herein, "wild type" refers to a dominant genotype which naturally occurs in the normal population of *P. syringae* (i.e., strains or isolates of *P. syringae* that are found in nature and not produced by laboratory manipulation). As is the case with other organisms, the characteristics of the pseudomycin A' and/or B' producing cultures employed in this invention, *P. syringae* strains such as MSU 174, MSU 16H, MSU 206, 25-B1, 7H9-1, and 67 H1 are subject to variation. Thus, progeny of these strains, e.g., recombinants, mutants and variants, may be obtained by methods well-known to those skilled in the art.

Mutant strains of *P. syringae* are also suitable for production of pseudomycin A' and/or B'. As used herein, mutant refers to a sudden heritable change in the phenotype of a strain, which can be spontaneous or induced by known mutagenic agents, including radiation and various chemicals. Mutant *P. syringae* of the present invention can be produced using a variety of mutagenic agents including radiation such as ultraviolet light, x-rays; chemical mutagens, site-specific mutagenesis, and transposon mediated mutagenesis. Examples of chemical mutagens are ethyl methanesulfonate (EMS), diepoxyoctane, N-methyl-N-nitro-N'-nitrosoguanine (NTG), and nitrous acid.

Pseudomycin A' and/or B' producing mutants of *P. syringae* of the present invention can be produced by treating the bacteria with an amount of a mutagenic agent effective to produce mutants that overproduce pseudomycin A' and/or B', that produce pseudomycin A' and/or B' in excess over other pseudomycins, or that produce pseudomycin A' and/or B' under advantageous growth conditions. While the type and amount of mutagenic agent to be used can vary, a preferred method is to serially dilute NTG to levels ranging from 1 to 100 $\mu$g/ml. Preferred mutants of the invention are those that overproduce pseudomycin A' and/or B' grow in minimal defined media. The mutants overproduce pseudomycin A' and/or B' preferably to at least about 10 $\mu$g/mL.

Environmental isolates, mutant strains, and other desirable strains of *P. syringae* can be subjected to selection for desirable traits of growth habit, growth medium, nutrient source, carbon source, growth conditions, and amino acid requirements. Preferably, a pseudomycin A' and/or B' producing strain of *P. syringae* is selected for growth on minimal defined medium, such as N21 medium, and/or for production pseudomycin A' and/or B' at levels greater than about 10 $\mu$g/mL. Preferred strains exhibit the characteristic of producing pseudomycin A' and/or B' when grown on a medium including glycine and, optionally, either a lipid, a potato product, or a combination thereof.

Recombinant strains can be developed by transforming the *P. syringae* strains, using established laboratory procedures well-known to those skilled in the art. Through the use of recombinant technology, the *P. syringae* strains can be transformed to express a variety of gene products in addition to the antibiotics these strains produce. For instance, one can transform the strains with a recombinant vector that confers resistance to an antibiotic to which the strains are normally sensitive. Transformants thus obtained will produce not only pseudomycins, such as pseudomycins A' and/or B', but also the resistance-conferring enzyme that allows selection of the transformed from wild-type cells. Furthermore, using similar techniques, one can modify the present strains to introduce multiple copies of the endogenous pseudomycin-biosynthesis genes to achieve greater pseudomycin, such as pseudomycin A' and/or B' yield. Progeny, i.e. natural and induced variants, mutants and recombinants, of the *P. syringae* strains 25-B1, 67H1, and 7H9-1 which retain the characteristic of pseudomycin, such as pseudomycin A' and/or B' overproduction are part of this invention.

Growth of *Pseudomonas syringae*

As described herein, "aqueous nutrient media" refers to a water-base composition including minerals and organic compounds and their salts necessary for growth of the bacterium used in the present invention. Preferred nutrient media contain an effective amount of three or fewer amino acids, preferably, glutamic acid, glycine, histidine or a combination thereof. In one embodiment, the medium contains an effective amount of glycine and, optionally, one or more of a potato product and a lipid. Glycine can be provided as a single amino acid or as part of a mixture of amino acids, such as hydrolyzed protein. Suitable lipids include soybean oil, or a fatty acid. Suitable potato products include potato dextrose broth, potato dextrin, potato protein, and commercial mashed potato mix food product. Preferred minerals in the nutrient medium include salt mixtures typically used in cell culture and fermentation, such as Czapek mineral salts solution (e.g., KCl, $MgSO_4$, and $FeSO_4$). The organic compound in the nutrient media preferably includes glucose and can optionally include soluble starch; other like organic compounds can also be included. The pH of the medium is preferably between about 4 and 6.5, more preferably about 4.5 to about 5.7, most preferably about 5.2.

Although the amount of each ingredient in the nutrient broth is not typically critical to growth of the bacteria or to production of pseudomycin A' and/or B' certain levels of nutrients are advantageous. A preferred amount of glycine is about 0.1 g/L to about 10 g/L, more preferably about 0.3 g/L to about 3 g/L, most preferably about 1 g/L. A preferred amount of lipid is about 1 g/L to about 10 g/L of an oil product such as soybean oil, more preferably about 0.5 g/L to about 2 g/L of soybean oil. A preferred amount of a fatty acid or fatty acid ester is about 0.5 g/L to about 5 g/L. Preferred amounts of potato products include about 12 g/L to about 36 g/L, preferably about 24 g/L of potato dextrose broth; about 5 g/L to about 50 g/L, preferably about 30 g/L of commercial mashed potato mix; about 1 g/L to about 30 g/L, preferably about 20 g/L of potato dextrin; or about 1 g/L to about 10 g/L, preferably about 4 g/L of potato protein. A preferred nutrient medium includes minerals, preferably, KCl at about 0.02 to about 2 g/L, more preferably about 0.2 g/L; $MgSO_4$, preferably $MgSO_4.7H_2O$, at about 0.02 to about 2 g/L, more preferably about 0.2 g/L; and $FeSO_4$, preferably $FeSO_4.7H_2O$, at about 0.4 to about 40 mg/L, more preferably about 4 mg/L. When present, soluble starch is preferably at about 0.5 to about 50 g/L, more preferably about 5 g/L. Glucose is preferably present at about 2 to about 80 g/L, more preferably about 20 g/L.

*P. syringae* are typically grown in the media described under conditions of controlled or regulated pH, and temperature. *P. syringae* grow and pseudomycin A' and/or B' at temperatures between about 15° C. and about 35° C., preferably about 20° C. to about 30° C., more preferably about 22° C. to about 27° C., most preferably about 25° C. *P. syringae* grow and produce pseudomycin A' and/or B' at pH between about 4 and about 9, preferably about 4 and about 6, more preferably about 4.5 to about 5.5. Typically growth of *P. syringae* does not occur when the temperature is above 37° C. or below 10° C. or when the pH is above 9 or below 4.

Method for Production of Pseudomycins A' and B'

To produce pseudomycin A' and/or B' from a wild type or mutant strain of *P. syringae,* the organism is cultured with agitation in an aqueous nutrient medium including an effective amount of three or fewer amino acids. The three or fewer amino acids are preferably glutamnic acid, glycine, histidine, or a combination thereof. In one preferred embodiment, the amino acids include glycine and, optionally, one or more of a potato product and a lipid. Culturing is conducted under conditions effective for growth of *P. syringae* and production of pseudomycin A' and/or B'. Effective conditions include temperature of about 22° C. to about 27° C., and a duration of about 36 hours to about 96 hours. When cultivated on the media such as those described herein, *P. syringae* can grow in cell densities up to about 10–15 g/L dry weight and produce pseudomycins A' and/or B' in total amounts at least about 10 $\mu$g/mL.

Controlling the concentration of oxygen in the medium during culturing of *P. syringae* is advantageous for production of pseudomycin A' and/or B'. Preferably, oxygen levels are maintained at about 5% to about 50% saturation, preferably about 30% saturation. Sparging with air, with pure oxygen, or with gas mixtures including oxygen can regulate the concentration of oxygen in the medium. Further, adjustment of the agitation rate can be used to adjust the oxygen transfer rate.

Controlling the pH of the medium during culturing of *P. syringae* is advantageous for production of a pseudomycin A' and/or B'. Pseudomycins, such as pseudomycins A' and/or B', are labile at basic pH, and significant degradation can occur if the pH of the culture medium is above about 6 for more than about 12 hours. Preferably, the pH of the culture medium is maintained at less than about 6, preferably less than about 5.5, and preferably above 4.0. The pH is preferably maintained at about 5 to about 5.4, more preferably about 5.0 to about 5.2. Although not limiting to the present invention, it is believed that pseudomycin degradation at basic pH is due to opening of the lactone ring and conversion of ClThr to Thr.

*P. syringae* can produce pseudomycins A' and/or B' when grown in batch culture. However, fed-batch or semi-continuous feed of glucose and, optionally, an acid or base, such as ammonium hydroxide, to control pH, enhances pseudomycin production. Pseudomycin production by *P. syringae* can be further enhanced by using continuous culture methods in which glucose and, optionally, an acid or base, such as ammonium hydroxide, to control pH, are fed automatically.

Pseudomycins A' and/or B' can be detected, determined, isolated, and/or purified by any of a variety of methods known to those of skill in the art. For example, the level of pseudomycin activity in a broth or in an isolated or purified composition can be determined by antifungal action against a fungus such as Candida. Numerous methods are known for the preparation and analysis of the pseudomycins. For example, one or more pseudomycins can be isolated and purified by chromatography, such as HPLC.

Pharmaceutical Uses

Formulations and Antifungal Action of Pseudomycin A' or B'

Each of pseudomycin A' and B' show in vitro and in vivo activity and therefore may useful in combating either systemic fungal infections or fungal skin infections. Accordingly, the present invention provides a method of inhibiting fungal activity including contacting pseudomycin A' and/or B' or a pharmaceutically acceptable salt thereof with a fungus. A preferred method includes inhibiting growth or activity of various fungi including *C. parapsilosis, C. albicans, Cryptococcus neoformans,* and *Histoplasma capsulatum.* As used herein contacting a compound of the invention with a parasite or fungus refers to a union or junction, or apparent touching or mutual tangency of a compound of the invention with a parasite or fungus. However, the term contacting does not imply any mechanism of inhibition.

The present invention further provides a method of treating a fungal infection which includes administering an effective amount of pseudomycin A' and/or B', or a pharmaceutically acceptable salt, hydrate, or ester thereof, to a host in need of such treatment. A preferred method includes treating an infection by various fungi including *C. parapsilosis, C. albicans, Cryptococcus neoformans,* and *Histoplasma capsulatum.* When administered in an effective and appropirate amount, a formulation of pseudomycin A' and/or B' reduces the burden of a fungal infection, reduces symptoms associated with the fungal infection, and can result in the elimination of the fungal infection.

Some patients in need of antifungal therapy have severe symptoms of infection, such as high fever, and are likely to be in intensive or critical care. Various fungi can cause such serious infections. Candida spp., for example, may cause mucosal and serious systemic infections. Azole and polyene resistant strains of Candida have been reported with increasing frequency. Aspergillus causes life-threatening systemic infections. Cryptococcus is responsible for meningitis. Such serious fungal infections may occur in immune compromised patients, such as those receiving organ or bone marrow transplants, undergoing chemotherapy for cancer, recovering from major surgery, or suffering from HIV infection. For such patients, antifungal therapy would typically include intravenous administration of a formulation containing pseudomycin A' and/or B' over several days or more to halt the infection.

With respect to antifungal activity, the term "effective amount," means an amount of a compound of the present invention which is capable of inhibiting fungal growth or activity, or reducing symptoms of the fungal infection. For most fungal infections reduction of symptoms of the infection includes reduction of fever, return to consciousness, and increased well being of the patient. Preferably, symptoms are reduced by killing the fungus to eliminate the infection or to bring the infection to a level tolerated by the patient or controlled by the patient's immune system. As used herein inhibiting refers to inhibiting fungal activity, including stopping, retarding or prophylactically hindering or preventing the growth or any attending characteristics and results from the existence of a fungus.

The dose administered will vary depending on such factors as the nature and severity of the infection, the age and general health of the host and the tolerance of the host to the antifungal agent. Typically, the compositions will be administered to a patient (human or other animal, including mammals such as, but not limited to, cats, horses and cattle and avian species) in need thereof, in an effective amount to inhibit the fungal infection. The particular dose regimen likewise may vary according to such factors and may be given in a single daily dose or in-multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg. For serious infections, the compound can be administered by intravenous infusion using, for example, 0.01 to 10 mg/kg/hr of the active ingredient.

The present invention also provides pharmaceutical formulations useful for administering the antifungal compounds of the invention. Accordingly, the present invention also provides a pharmaceutical formulation including one or more pharmaceutically acceptable carriers, diluents, vehicles, excipients, or other additives and pseudomycin A' and/or B'. The active ingredient in such formulations includes from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

The formulation can include additives such as various oils, including those of petroleum, animal, vegetable or synthetic origin, for example, peanut oil, soybean oil, mineral oil, and sesame oil. Suitable pharmaceutical excipients include starch, cellulose, glucose, lactose, sucrose, gelatin, malt, magnesium stearate, sodium stearate, glycerol monostearate, sodium chloride, dried skim milk, glycerol, propylene glycol, water, and ethanol. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, and buffers. Suitable pharmaceutical carriers and their formulations are described in Martin, "Remington's Pharmaceutical Sciences," 15th Ed.; Mack Publishing Co., Easton (1975), see, e.g., pp. 1405–1412 and pp. 1461–1487.

The term "pharmaceutically acceptable salt", as used herein, refers to salts of the compounds described above that are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, and phosphoric acid, and organic acids such as p-toluenesulfonic, methanesulfonic acid, oxalic acid, p-bromophenylsulfonic acid, carbonic acid, succinic acid, citric acid, benzoic acid, and acetic acid. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, napththalene-2-sulfonate, and mandelate. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, and bicarbonates. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, and calcium carbonate. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Pseudomycin A' and/or B' may be administered parenterally, for example using intramuscular, subcutaneous, or intraperitoneal injection, nasal, or oral routes. In addition to these methods of administration, pseudomycin A' and/or B' may be applied topically for superficial skin infections, or eradication or inhibition of fungi in the mucus.

For parenteral administration the formulation includes pseudomycin A' and/or B' and a physiologically acceptable diluent such as deionized water, physiological saline, 5% dextrose and other commonly used diluents. The formulation may contain a cyclodextrin and/or a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, and sterile packaged powders.

For oral administration, the antifungal compound is filled into gelatin capsules or formed into tablets. Such tablets may also contain a binding agent, a dispersant or other suitable excipients suitable for preparing a proper size tablet for the dosage pseudomycin A' and/or B'. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and pseudomycin A' and/or B' in an amount of from about 2.5 to about 40 mg/ml.

For topical use the antifungal compound may be formulated with a dry powder for application to the skin surface or it may be formulated in a liquid formulation including a solubilizing aqueous liquid or non-aqueous liquid, e.g., an alcohol or glycol.

Uses of Formulations of Pseudomycin A' or B'

The present invention also encompasses a kit including the present pharmaceutical compositions and to be used with the methods of the present invention. The kit can contain a vial which contains a formulation of the present invention and suitable carriers, either dried or in liquid form. The kit further includes instructions in the form of a label on the vial and/or in the form of an insert included in a box in which the vial is packaged, for the use and administration of the compounds. The instructions can also be printed on the box in which the vial is packaged. The instructions contain information such as sufficient dosage and administration information so as to allow a worker in the field to administer the drug. It is anticipated that a worker in the field encompasses any doctor, nurse, or technician who might administer the drug.

The present invention also relates to a pharmaceutical composition including a formulation of pseudomycin A' and/or B' and that is suitable for administration by injection. According to the invention, a formulation of pseudomycin A' and/or B', can be used for manufacturing a composition or medicament suitable for administration by injection. The invention also relates to methods for manufacturing compositions including a formulation of pseudomycin A' and/or B' in a form that is suitable for administration by injection. For example, a liquid or solid formulation can be manufactured in several ways, using conventional techniques. A liquid formulation can be manufactured by dissolving pseudomycin A' and/or B', in a suitable solvent, such as water, at an appropriate pH, including buffers or other excipients.

Agricultural Uses

Antibiotics produced from *P. syringae* NRRL B-12050 have been demonstrated to effectively treat Dutch elm disease, (see, e.g., U.S. Pat. Nos. 4,342,746 and 4,277,462). In particular, *P. syringae* MSU 16H has been shown to confer a greater protection than the wild-type strain in elms infected with *Ceratocystis ulmi,* the causal agent of Dutch elm disease, (see e.g., Lam et al. *Proc. Natl. Sci. USA,* 84, 6447–6451 (1987)). More extensive tests on field-grown elms confirmed the phenomenon of biocontrol at the prophylactic level. Hence, the pseudomycins of the present invention may be useful as a preventative treatment for Dutch Elm disease. The pseudomycins have been shown to be toxic to a broad range of plant-pathogenic fungi including *Rynchosporium secalis, Ceratocystis ulmi, Rizoctonia solani, Sclerotinia sclerotiorum, Verticillium albo-atrum, Verticillium dahliae, Thielaviopis basicola, Fusarium oxysporum* and *Fusarium culmorum,* (see Harrison, L., et al., "Pseudomycins, a family of novel peptides from *Pseudomonas syringae* possessing broad-spectrum antifungal activity," *J. General Microbiology,* 7, 2857–2865 (1991).) Consequently, the isolated pseudomycin A' and/or B' (including hydrates, solvates, and esters thereof) may be useful in the treatment of fungi in plants (in particular, *V. albo-atrum, Rhizoctonia solani* and *F. oxysporum*) either as a direct treatment or preventative treatment. Generally, the infected plants are treated by injecting or spraying an aqueous suspension of the pseudomycin compounds into or onto the plant. Means of injection are well-known to those skilled in the art (e.g., gouge pistol). Any means of spraying the suspension may be used that distributes an effective amount of the active material onto the plant surface. The suspension may include other additives generally used by those skilled in the art, such as solubilizers, stabilizers, wetting agents, and combinations thereof.

Treatment of the plant may also be accomplished using a dry composition containing the isolated pseudomycin A' and/or B' compounds. The dry formulation may be applied to the plant surface by any means well-known to those skilled in the art, such as spraying or shaking from a container.

The present invention may be better understood with reference to the following examples. These examples are intended to be representative of specific embodiments of the invention, and are not intended as limiting the scope of the invention.

EXAMPLES

Biological Materials on Deposit

*P. syringae* MSU 16H is publicly available from the American Type Culture Collection, Parklawn Drive, Rockville, Md., USA as Accession No. ATCC 67028. *P. syringae* strains 25-B1, 7H9-1, and 67 H1 were deposited with the American Type Culture Collection on Mar. 23, 2000 and were assigned the following Accession Nos.:

25-B1 Accession No. PTA-1622
7H9-1 Accession No. PTA-1623
67 H1 Accession No. PTA-1621

Example 1

Production of Pseudomycins A' and B'

Fermentation methods were developed for producing pseudomycin A' and/or B' in the fermentation broth of a *Pseudomonas syringae* strain.

Materials and Methods

Preparation of Inoculum

An aliquot of cells stored in the vapor phase of liquid nitrogen was thawed and used to inoculate two 900 mL portions of CSM broth. CSM broth was composed of (g/L): dextrose (5), maltose (4), Difco Tryptic Soy Broth (30), Difco yeast extract (3), and $MgSO_4$ $7H_2O$ (2). Approximately 0.5 mL of cells was used to inoculate each 900 mL portion of medium contained in a two liter flask. Flasks were incubated with shaking for 24 hours at 25° C. The contents of two flasks were combined to inoculate a 150 liter fermentor containing 115 liters of sterile fermentation broth.

Fermentation Stage

Fermentation broth was composed of (g/L): dextrose (20), soluble starch (5), Basic American Foods Country Style Potato Pearls instant mashed potatoes (30), glycine (1), $MgSO_4$ $7H_2O$ (0.2), KCl (0.2), and $FeSO_4$ $7H_2O$ (0.004) in tap water. The pH was adjusted to 5.2 before sterilization. Fermentation was carried out at 25° C. for 68 hr. Dissolved oxygen was maintained at or above 30% of air saturation by continuous adjustment of air flow and impeller agitation rate. The pH was maintained between 4.0 and 5.4 through the addition of either $H_2SO_4$ or NaOH.

Variations on the Batch Methods

Several variations of the simple batch process were also found to produce pseudomycins A' and/or B'. Dextrose can be fed to the fermentors starting 24 hours after initial inoculation at a rate of 60 mL per hour. Feeding can be continued throughout the course of the fermentation. Alternatively, a process has been used where dissolved oxygen is maintained at 5% of air saturation starting 24 hours after inoculation and continuing until the end of the fermentation period. Maintenance of dissolved oxygen at 5% was achieved through addition of inert nitrogen gas ($N_2$) to the air supply leading to the fermentor. In all cases, gas was supplied through a single submerged sparger tube with an opening positioned just below the bottom agitator turbine in the fermentor.

Results and Conclusions

Several fermentation methods produce pseudomycin A' and/or B' from *P. syringae.*

Example 2

Isolation and Purification of Pseudomycins A' and B'

Methods were developed for isolation and purification pseudomycins A' and B' from the fermentation broth of a *Pseudomonas syringae* strain.

Materials and Methods

The whole fermentation broth (4×100 L) after harvest was filtered through a Membralox ceramic filter (0.45 μm) to afford a filtrate (fraction A) and a solid slurry (fraction B). Fraction B (135 L) was extracted with an equal volume of acetone containing 0.1% TFA for 120 min and allowed to settle. The clear acetone extract was separated by filtration and then evaporated in vacuo to an aqueous solution to yield fraction C (88 L). First, fraction A was charged on to a HP20ss resin column (10 L) packed in water and the column was washed with 15% acetonitrile containing 0.1% TFA (20 L). Fraction C was then loaded on to the same column and the column was washed with 20 L of 15% acetonitrile containing 0.1% TFA as before.

The column was then eluted with a linear gradient of 15–20% acetonitrile containing 0.1% TFA over 30 min and 20–35% acetonitrile containing 0.1% TFA over 60 min with 1 L/min flow rate. One liter fractions were collected. Fractions 6–9 were combined (4 L) to yield fraction D (24 g). A portion of fraction D (~1 g) was chromatographed over a reversed-phase column (Dynamax $C_{18}$ 41.4×250 mm) using triethylammonium phosphate buffer (pH 3)-acetonitrile-methanol as mobile phase (65:17:18 to 30:35:35 gradient elution over 45 min with 40 ml/min flow rate). Appropriate fractions were combined, volume was reduced to 75 ml and rechromatographed over a $C_{18}$ column as before using a gradient 80:10:10 to 46:27:27 to afford fraction E (113 mg) and fraction F (116 mg). Further chromatography of fractions E and F over a $C_{18}$ column (Dynamax 21.4×250 mm) furnished 45 mg pseudomycin A' and 62 mg of pseudomycin B', respectively.

Results and Conclusions

HPLC methods similar to those used to purify other pseudomycins resulted in purification of pseudomycins A' and B' from fermentation broth.

Example 3

Determination of the Structure of Pseudomycins A' and B'

Mass spectrometry and NMR determined the structures pseudomycins A' and B'.

Structure Determination of Pseudomycin A'

Methods and Results

The molecular formula of pseudomycin A' was determined by high resolution FABMS as $C_{52}H_{89}ClN_{12}O_{20}$ [m/z 1237.6112 for $C_{52}H_{90}ClN_{12}O_{20}$ $(M+H)^+$, Δ-2.4 ppm]. When compared to pseudomycin A the molecular formula of pseudomycin A' showed one additional $CH_2$ group. This observation suggested that in pseudomycin A' the N-terminal serine may be acylated with 3,4-dihydroxypentadecanoic acid instead of 3,4-dihydroxytetradecanoic acid as in pseudomycin A. This argument is supported by the fact that in all previously characterized pseudomycins, the core possess a distinctive and identical nonadepsipeptide ring and the only difference among them arise due to the nature of the hydrophobic side chain.

Accordingly the NMR spectral data of pseudomycin A' is virtually identical to all the known pseudomycins, such as pseudomycin A, B, C and C'. Comprehensive analysis of $^1H$, $^{13}C$, and 2D NMR spectra including TOCSY and HMQC of pseudomycin A' established 3.4 diol functionality in the hydrophobic side chain of pseudomycin A' and enabled assignment of all the protons and proton bearing carbons in the molecule (Table 1). The structure determined for pseudomycin A' based on these mass spectrometric and NMR data is shown below.

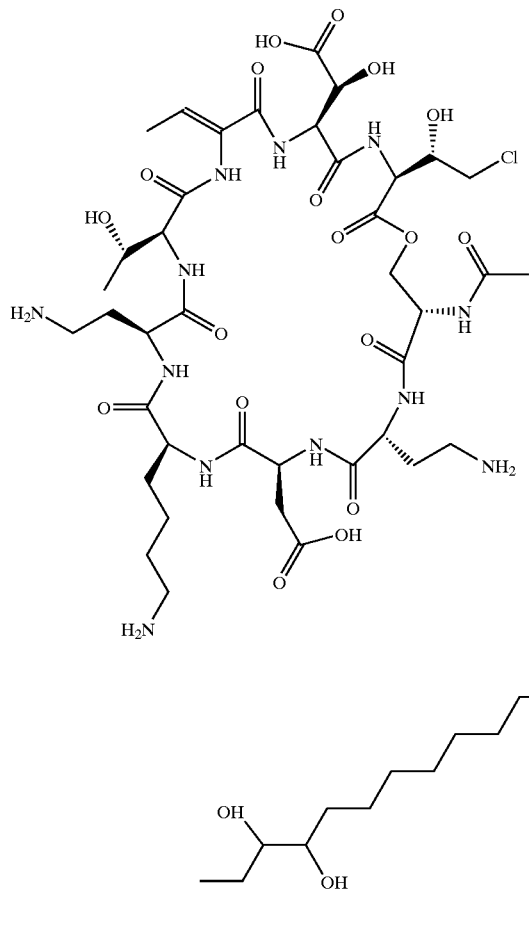

Structure of Pseudomycin A' Derived from Mass and NMR Spectral Data

TABLE 1

$^{1}$H and $^{13}$CNMR data of Pseudomycin A' in $H_2O$ + $CD_3CN$

| Amino acid | Position | $\delta_H$ | $\delta_C$ |
|---|---|---|---|
| Ser | NH | 8.28 | — |
| | α | 4.59 | 54.0 |
| | β1 | 4.50 | 65.5 |
| | β2 | 4.41 | |
| Dab-1* | NH | 8.48 | — |
| | α | 4.15 | 53.1 |
| | β1 | 1.98 | |
| | γ | 2.91 | 37.4 |
| | NH$_2$ | 7.50 | — |
| Asp | NH | 8.34 | — |
| | α | 4.54 | 51.5 |
| | β1 | 2.86 | 36.0 |
| | β2 | 2.80 | |
| Lys | NH | 7.80 | — |

TABLE 1-continued $^{1}$H and $^{13}$CNMR data of Pseudomycin A' in $H_2O$ + $CD_3CN$

| Amino acid | Position | $\delta_H$ | $\delta_C$ |
|---|---|---|---|
| | α | 4.16 | 54.6 |
| | β | 1.75 | 30.8 |
| | γ1 | 1.31 | 23.2 |
| | γ2 | 1.22 | |
| | δ | 1.54 | 27.2 |
| | ε | 2.83 | 40.4 |
| | NH$_2$ | 7.34 | — |
| Dab-2* | NH | 8.09 | — |
| | α | 4.28 | 52.1 |
| | β1 | 2.11 | 28.7 |
| | β2 | 1.96 | |
| | γ | 2.89 | 37.6 |
| | NH$_2$ | | — |
| Thr | NH | 7.63 | — |
| | α | 4.28 | 59.8 |
| | β | 3.92 | 68.6 |
| | γ | 1.16 | 20.4 |
| Dhb | NH | 9.45 | — |
| | β | 6.49 | 133.9 |
| | γ | 1.69 | 13.5 |
| Hyd. Asp | NH | 7.85 | — |
| | α | 4.94 | 56.9 |
| | β | 4.78 | 71.6 |
| ClThr | NH | 7.88 | |
| | α | 4.87 | 56.0 |
| | β | 4.31 | 72.3 |
| | γ1 | 3.50 | 45.6 |
| | γ2 | 3.42 | |
| Side chain | 2a | 2.47 | 39.4 |
| | 2b | 2.30 | |
| | 3 | 3.76 | 72.6 |
| | 4 | 3.39 | 75.1 |
| | 5 | 1.41 | 33.3 |
| | 6–14 | 1.21 | 32.4, 30.2X4, 29.9, 27.2. 26.4, 23.2 |
| | 15 | 0.81 | 14.3 |

*The assignments due to Dab-1 and Dab-2 may be interchanged

Structure Determination of Pseudomycin B'

The structure determination of pseudomycin B' was again accomplished through the interpretation of mass and NMR spectral data. The molecular formula $C_{49}H_{83}ClN_{12}O_{19}$ [m/z 1179.5685 for $C_{49}H_{84}ClN_{12}O_{19}$ (M+H)$^+$, Δ-1.8 ppm] was established by high resolution FAB-MS data. This formula showed two $CH_2$ less than that observed for pseudomycin B. Detailed analysis of $^{1}$H. $^{13}$C and 2D NMR including TOCSY and HMQC spectra and comparison of the spectral data with those of known pseudomycins again revealed identical amino acid composition. In addition the NMR data indicated the presence of 3-hydroxydodecanoic acid (Table 2). Thus, from this spectral data, the structure of pseudomycin B' is derived as shown below.

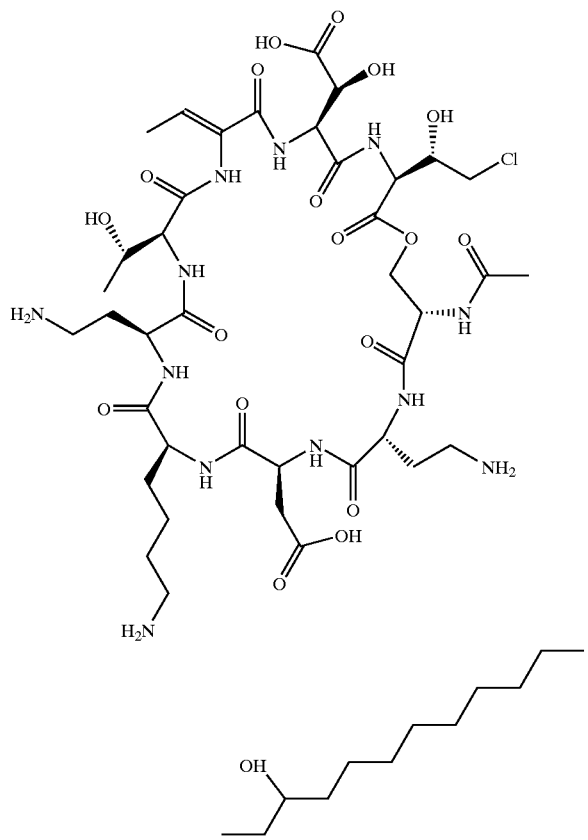

Structure of Pseudomycin B' Derived from Mass and NMR Spectral Data

TABLE 2

| $^1$H and $^{13}$CNMR data of Pseudomycin B' in H$_2$O + CD$_3$CN | | | |
|---|---|---|---|
| Amino acid | Position | $\delta_H$ | $\delta_C$ |
| Ser | NH | 8.31 | — |
|  | α | 4.64 | 53.5 |
|  | β1 | 4.54 | 65.8 |
|  | β2 | 4.35 |  |
| Dab-1* | NH | 8.52 | — |
|  | α | 4.13 | 53.3 |
|  | β1 | 2.02 | 28.7 |
|  | β2 |  |  |
|  | γ | 2.94 | 37.3 |
|  | NH$_2$ | 7.54 | — |
| Asp | NH | 8.30 | — |
|  | α | 4.56 | 51.6 |
|  | β1 | 2.86 | 36.0 |
|  | β2 | 2.80 |  |
| Lys | NH | 7.90 | — |
|  | α | 4.09 | 54.9 |
|  | β | 1.75 | 29.8 |
|  | γ1 | 1.28 | 23.2 |
|  | γ2 | 1.18 |  |
|  | δ | 1.52 | 27.3 |
|  | ε | 2.82 | 40.4 |
|  | NH$_2$ | 7.34 | — |
| Dab-2* | NH | 8.24 |  |
|  | α | 4.35 | 51.8 |
|  | β1 | 2.12 | 29.2 |
|  | β2 | 1.99 |  |
|  | γ | 2.90 | 37.7 |
|  | NH$_2$ |  | — |
| Thr | NH | 7.75 | — |
|  | α | 4.23 | 60.4 |

TABLE 2-continued

| $^1$H and $^{13}$CNMR data of Pseudomycin B' in H$_2$O + CD$_3$CN | | | |
|---|---|---|---|
| Amino acid | Position | $\delta_H$ | $\delta_C$ |
|  | β | 3.93 | 68.2 |
|  | γ | 1.18 | 20.5 |
| Dhb | NH | 9.45 | — |
|  | β | 6.57 | 134.8 |
|  | γ | 1.68 | 13.7 |
| Hyd. Asp | NH | 7.79 | — |
|  | α | 4.95 | 57.1 |
|  | β | 4.71 | 72.0 |
| ClThr | NH | 7.98 |  |
|  | α | 4.87 | 55.8 |
|  | β | 4.31 | 72.5 |
|  | γ1 | 3.48 | 45.6 |
|  | γ2 | 3.42 |  |
| Side chain | 2a | 2.33 | 43.8 |
|  | 2b | 2.24 |  |
|  | 3 | 3.85 | 69.6 |
|  | 4 | 1.37 | 37.6 |
|  | 5–11 | 1.20 | 32.4, 30.1, 30.1, 29.8, 23.2 |
|  | 12 | 0.81 | 14.4 |

*The assignments due to Dab-1 and Dab-2 may be interchanged

Conclusions

Pseudomycins A' and B' represent new members of a unique class of nonadepsipeptides. Although these molecules are very closely related to the known pseudomycins differing only in the nature of the hydrophobic side chain, they should play a key role in elucidating the structure-activity relationship among this class of compounds as antifungals.

Example 4

Isolation, Characterization and Mutagenesis of *Pseudomonas syringae*

Environmental isolates and mutants of *P. syringae* were produced and employed in production of antifungal agents.

Materials and Methods

Strains MSU 174 and MSU 16-H were isolated and characterized as described in U.S. Pat. No. 5,576,298, issued Nov. 19, 1996 to G. Strobel et al.; Harrison et al., "Pseudomycins, a family of novel peptides from *Pseudomonas syringae* possessing broad-spectrum antifungal activity." *J. Gen. Microbiology* 137, 2857–2865 (1991); and Lamb et al., "Transposon mutagenesis and tagging of fluorescent pseudomonas: Antimycotic production is necessary for control of Dutch elm disease," *Proc. Natl. Acad. Sci. USA* 84, 6447–6451 (1987). The disclosures of the references cited in this paragraph are incorporated herein by reference.

Additional strains were derived from such wild type and transposon generated mutants by chemical mutagenesis. Strains subjected to mutagenesis include MSU 174. MSU 16H, and 25-B1. The strain to be mutagenized was grown in CSM medium, then divided into the medium including 0, 1, 2, 4, 16, or 32 μg/mL of the chemical mutagen 1-methyl-3-nitro-1-nitrosoguanidine (NTG or MNNG). These cells were then frozen for future screening and selection.

Mutagenized cells were selected for desirable growth conditions and/or production of one or more Pseudomycins, such as pseudomycin A' and/or B'. Chemically mutagenized cells of *P. syringae*, such as mutagenized strain 25-B1, were thawed and diluted to 6 cells/mL in N21SM medium (Table 5). This medium sometimes contained one or more components for selection, such as varying concentrations of phosphate. A 50 μL volume of mutagenized cells was dispensed into a well of a 96-well round bottom microtiter plate for a delivery of an average of 0.3 cells/well. Typically, silicone oil was added to each well to minimize evaporation. The plates were incubated with shaking for 6 to 12 days at 25° C.

TABLE 5

The Composition of N21SM Medium

| INGREDIENT | GRAMS PER LITER |
| --- | --- |
| Glucose | 20 |
| Ammonium Sulfate | 0.5 |
| Monosodium Glutamate or L-glutamic acid | 2 |
| L-Histidine | 2 |
| Glycine | 0.5 |
| Soluble Starch | 5 |
| $KH_2PO_4$ | 0.2 |
| Czapek Mineral Salts Solution | 2 mL |
| MES Buffer | 9.8 |
| Adjust pH to 5.0 | |

After this incubation, an aliquot, typically 5 TL, from each well was serially diluted (e.g. 1:56, 1:196, 1:320, 1:686, and/or 1:1715) and evaluated for activity against *Candida albicans* in a liquid microtiter plate bioassay. The plates were incubated at 37° C. overnight and the wells were scored for inhibition of *C. albicans* growth. Suitable strains were picked, inoculated into CSM medium (Table 6), and grown for 1 to 3 days at 25° C.

TABLE 6

Complete Streptomyces Medium (CSM)

| Component | Concentration (g/L) |
| --- | --- |
| Glucose | 5 |
| Maltose | 4 |
| Difco Tryptic Soy Broth | 30 |
| Difco Yeast Extract | 3 |
| $MgSO_4 \cdot 7H_2O$ | 2 |
| No pH adjustment | |

The selected strains were preserved and inoculated into fermentation bottles containing 13 mL of N21SM medium and grown for approximately 66 hours at 25° C. An aliquots was removed from this fermentation, extracted for 1 hour with a volume of acetonitrile equal to the volume of the aliquot, centrifuged, and decanted for HPLC analysis of one or more Pseudomycins, such as pseudomycin A' or B', as described in Examples 1–3. Strains producing one or more Pseudomycins, such as pseudomycin A' or B', were reisolated, refermented, and prepared for growth on a larger scale.

Results

Strains exhibiting production of one or more Pseudomycins, such as pseudomycin A' or B', were produced using the methods described above.

Conclusion

The selection methods and criteria disclosed herein are effective for producing strains of *P. syringae* that grow on minimal medium and produce one or more pseudomycins, such as pseudomycin A' or B'.

Example 5

Growth of *P. syringae* and Production of Pseudomycins

Fermentation of *P. syringae* in medium N21, which does not include any potato products used in published media for growth of *P. syringae*, produced pseudomycins at levels suitable for isolation.

Production of Pseudomycins in Shaken Flasks and N21 Medium

Materials and Methods

*P. syringae* were grown in 50 mL of N21 culture medium (Table 7) in a 250 mL flask. The culture was started with an aliquot of an inoculum of *P. syringae* MSU 16H and maintained at 25° C. and 70% humidity for 7 days with shaking at 250 rpm in an incubator. At the end of the incubation period 4 mL of the broth are removed from the flask and mixed with 6 mL of methanol containing 0.1% phosphoric acid. It is believed that low pH stabilizes the pseudomycins. Particulate matter is removed by filtration or centrifugation and the pseudomycins were determined by HPLC as described herein.

TABLE 7

The Composition of N21 Medium

| INGREDIENT | GRAMS PER LITER |
|---|---|
| Sucrose | 35 |
| Ammonium Sulfate | 0.5 |
| Monosodium Glutamate | 2 |
| L-Histidine | 2 |
| Glycine | 0.5 |
| Soluble Starch | 5 |
| $KH_2PO_4$ | 0.2 |
| Czapek Mineral Salts Solution | 2 mL |
| Yeast Extract | 1 |
| MES Buffer | 9.8 |
| Adjust pH to 5.2 | |

Production of pseudomycin by several strains of *P. syringae* was evaluated employing N21 medium with and without added methyl myristate. The strains of *P. syringae* evaluated included MSU 16H, 25-B1, 67H1, and 7H9-1.

Results

The various strains of *P. syringae* when grown with or without methyl myristate produced significant levels of one or more pseudomycins, for example more than 10 Tg/mL of one or more of pseudomycin A, pseudomycin B, and/or pseudomycin C. Methyl myristate stimulated pseudomycin production for certain strains.

Conclusions

Various strains of *P. syringae* produce commercially significant levels of pseudomycins in medium lacking potato products, and this production can be stimulated by methyl myristate.

Production of Pseudomycins at a Scale of 5,000 L Employing N21 Medium

The methods for producing pseudomycins employing a medium without added potato products was scaled up to a 5,000 liter level.

Materials and Methods

Vegetative-stage flasks containing complete streptomyces medium (CSM, Table 5) inoculated with a frozen *P. syringae* culture, typically strain 67H1, and were shaken at 250 rpm and 25° C. for 24 hours. After 24 hours of incubation of the vegetative-stage flasks, the contents of these flasks was used to inoculate bump-stage flasks. The bump-stage flasks included the CSM medium and were rotated at 250 rpm and held at 25° C. The bump-stage flasks were inoculated with about 0.45 mL of pooled culture from three or four vegetative-stage flasks. The bump stage flasks typically include about 900 mL of CSM in a non-baffled 2.5 L Tunair™ flask. Two bump-stage cultures in Tunair™ flasks were set for each fermentor. The bump-stage flasks were incubated for 16 hours.

Then, two of the bump-stage cultures were pooled by combining in an inoculation bazooka. These combined cultures were used to inoculate a tank containing the medium described in Table 15 that has been supplemented with an additional 3 g/L (for a total of 4 g/L) of glycine, 1 g/L of soybean oil, and 1 g/L of yeast extract. These large-scale cultures were grown at 25° C. for three to four days. During this growing period, dissolved oxygen was controlled at 30% of air saturation with agitation and air flow, pH was controlled at 5.2±0.2 by addition of sulfuric acid or sodium hydroxide as required. Eighteen hours after beginning the large-scale culture, a glucose feed was started at a rate of 200 mL/h. Twenty hours after the start of the large-scale culture, ammonium hydroxide feed was started at a rate of 20 mL/h. During this culture, the holdback pressure was 5 psig. The initial setting for agitation was 150 rpm and air flow is 0.5 scfm. If required, an anti-foam agent was added, as well. Certain variations on these conditions were tested as well. After the three to four days of large-scale culture, the *P. syringae* were harvested. Antifungal activity was measured as described in Example 6.

Results and Conclusions

Pseudomycins were produced in commercially significant amounts at the 5,000 L scale employing a medium free of added potato products.

Example 6

Determination and Purification of Pseudomycins

Detection and Quantification of Pseudomycins by Antifungal Activity

The presence or amount of a pseudomycin or mixture of pseudomycins can be determined by measuring the antifungal activity of a preparation. Antifungal activity was determined in vitro by obtaining the minimum inhibitory concentration (MIC) of the preparation using a standard agar dilution test or a disc-diffusion test. A preparation of one or more pseudomycins can be an extract of a cell culture, or a more purified mixture. A typical fungus employed in testing antifungal activity is *C. albicans*. Antifungal activity was considered significant when the test preparation caused 10–12 mm diameter zones of inhibition on *Candida albicans* x657 seeded agar plates.

The antifungal studies were conducted using a microtiter broth dilution assay according to National Committee for Clinical Laboratory Standards guidelines in 96 well microtiter plates. Sabourauds and dextrose broth was adjusted to contain $2.5\times10^4$ conida/ml. Test compound was dissolved in water and tested in two-fold dilutions starting with the highest concentration of 20 μg/ml. Plates were incubated at 35° C. for 48 hr. The results in Table 3 and 4 show the minimal inhibitory concentration (MIC) of the compound that completely inhibited growth compared to untreated growth controls.

TABLE 3

Antifungal Activity of Pseudomycin A'

| Organism | MIC (μ/ml) |
|---|---|
| *Candida albicans* | 2.5 |
| *C. parapsilosis* | 5.0 |
| *Cryptococcus neoformans* | 1.25 |
| *Aspergillus fumigatus* | >20 |
| *Histoplasma capsulatum* | 5.0 |

TABLE 4

Antifungal Activity of Pseudomycin B'

| Organism | MIC (μ/ml) |
|---|---|
| *Candida albicans* | 10 |
| *C. parapsilosis* | 10 |
| *Cryptococcus neoformans* | 1.25 |
| *Aspergillus fumigatus* | >20 |
| *Histoplasma capsulatum* | 1.25–5.0 |

Detection and Quantification of Pseudomycins by HPLC

A sample believed to contain one or more pseudomycins was clarified by filtration or centrifugation. The clarified mixture was chromatographed on a Zorbax RxC8 column (3.5 T particles 25×0.46 cm) with a flow rate of 1 ml/min. The column was eluted with 20–55% acetonitrile with 0.2% TFA linear gradient over 15 min and held at 55% acetonitrile with 0.2% TFA for 5 min. Typically, pseudomycin A' eluted at about 13.7 min. (822 sec) and pseudomycin B' eluted at about 12.4 min (822 sec). Pseudomycins were detected by absorbance at 215 nm and quantified by integration of UV peaks. A standard of each of the pseudomycins was employed for identification and quantification.

Example 7

Formulations Including Pseudomycin A' and/or B'

The following formulation examples are illustrative only and are not intended to limit the scope of the invention in any way. The term "active ingredient" means pseudomycin A' and/or B' or a pharmaceutically acceptable salt thereof.

Formulation 1

Hard gelatin capsules are prepared using the following ingredients:

| Ingredient | Quantity (mg/ capsule) |
|---|---|
| Active ingredient | 250 |
| Starch. dried | 200 |
| Magnesium stearate | 10 |
| Total | 460 mg |

Formulation 2

A tablet is prepared using the ingredients below. The components are blended and compressed to form tablets each weighing 665 mg.

| Ingredient | Quantity (mg/ capsule) |
|---|---|
| Active ingredient | 250 |
| Cellulose, microcrystalline | 400 |
| Silicon dioxide, fumed | 10 |
| Stearic acid | 5 |
| Total | 665 mg |

Formulation 3

An aerosol solution is prepared containing the following components. The active compound is mixed with ethanol and the mixture added to a portion of the propellant 22, cooled to −30° C., and transferred to a filling device. The required amount is then fed to a stainless steel container and diluted with the remainder of the propellant. The valve units are then fitted to the container.

| Component | Weight (g) |
|---|---|
| Active ingredient | 0.25 |
| Methanol | 27.75 |
| Propellant 22 (Chlorodifluoromethane) | 74.00 |
| Total | 100.00 |

Formulation 4

Tablets, each containing 60 mg of active ingredient, are made as follows:

| | |
|---|---|
| Active ingredient | 60 mg |
| Microcrystalline cellulose | 45 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C., and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2.000 mg |
| Total | 2.225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows. The solution of these ingredients generally is administered intravenously to a subject at a rate of 1 ml per minute.

| | |
|---|---|
| Active ingredient | 100 mg |
| Isotonic saline | 1.000 mg |

The invention has been described with reference to various specific and preferred embodiments and techniques. However, it should be understood that many variations and modifications may be made while remaining within the spirit and scope of the invention.

We claim:

1. An isolated pseudomycin comprising pseudomycin A' of formula:

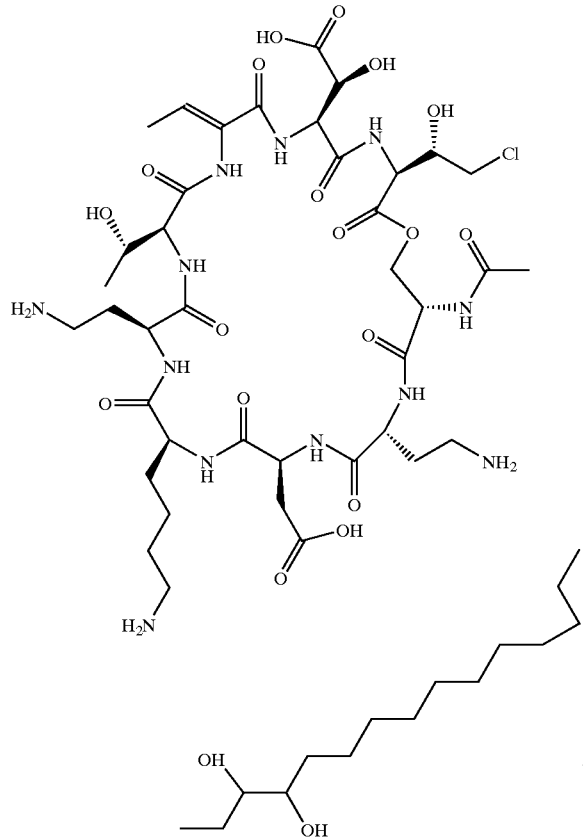

a pharmaceutically acceptable salt of pseudomycin A', a hydrate of pseudomycin A', or an ester of pseudomycin A'.

2. A method of inhibiting a fungus in or on a plant comprising contacting said plant with pseudomycin A' of formula:
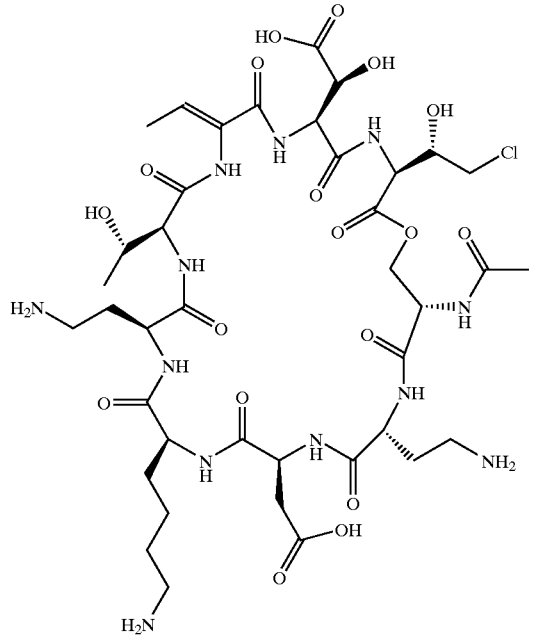
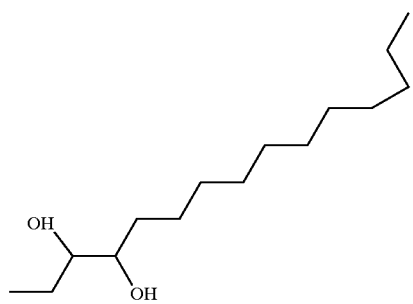
a pharmaceutically acceptable salt of pseudomycin A', a hydrate of pseudomycin A', or an ester of pseudomycin A'.
* * * * *